United States Patent [19]

Hilliard et al.

[11] Patent Number: 5,124,553
[45] Date of Patent: Jun. 23, 1992

[54] OPTICAL MEASUREMENT METHOD USING STACKED GERMANIUM AND SILICONE DETECTORS

[75] Inventors: Lorelli A. Hilliard; Evangelos Theocharous, both of Middlesex, England

[73] Assignee: The Standard Oil Company, Cleveland, Ohio

[21] Appl. No.: 602,901

[22] Filed: Oct. 24, 1990

Related U.S. Application Data

[63] Continuation of Ser. No. 233,630, Aug. 18, 1988, abandoned.

[30] Foreign Application Priority Data

Aug. 21, 1987 [GB] United Kingdom ............... 8719839
Oct. 17, 1987 [GB] United Kingdom ............... 8724374

[51] Int. Cl.$^5$ .................... G01N 21/17; G01N 21/59
[52] U.S. Cl. .................... 250/344; 250/343; 250/344; 250/301
[58] Field of Search .......... 250/343, 339, 344, 345, 250/301; 356/31

[56] References Cited

U.S. PATENT DOCUMENTS

| | | | |
|---|---|---|---|
| 2,790,081 | 4/1957 | Munday | 250/343 |
| 2,852,693 | 9/1958 | Hughes et al. | 250/301 |
| 3,729,264 | 4/1973 | Simazaki et al. | 357/206 |
| 3,962,578 | 6/1976 | Roschen | 250/226 |
| 4,286,327 | 8/1981 | Rosenthal et al. | 364/498 |
| 4,296,324 | 10/1981 | Kern et al. | 250/339 |
| 4,297,579 | 10/1981 | Spaeth | 250/343 |
| 4,383,181 | 5/1983 | Roess et al. | 250/573 |
| 4,391,253 | 7/1983 | Ito | 123/478 |
| 4,567,366 | 1/1986 | Shinohara | 250/339 |
| 4,577,970 | 3/1986 | Meserol | 356/440 |
| 4,587,427 | 5/1986 | Talbot et al. | 250/339 |
| 4,594,510 | 6/1986 | Brown et al. | 250/343 |
| 4,594,968 | 6/1986 | Degobert et al. | 123/1 |
| 4,596,931 | 6/1986 | Ehnholm et al. | 250/343 |
| 4,647,776 | 3/1987 | Kern et al. | 250/339 |
| 4,749,274 | 6/1988 | Aoki et al. | 356/136 |
| 4,770,129 | 9/1988 | Miyata et al. | 123/1 A |
| 4,771,176 | 9/1988 | Schiefer et al. | 250/343 |
| 4,772,790 | 9/1988 | Aldridge | 250/343 |
| 4,808,825 | 2/1989 | Miyatake et al. | 250/343 |

FOREIGN PATENT DOCUMENTS

| | | |
|---|---|---|
| 0245512 | 11/1986 | European Pat. Off. . |
| 1040046 | 3/1963 | United Kingdom . |
| 2008745A | 11/1978 | United Kingdom . |
| 2053466A | 6/1980 | United Kingdom . |
| 2136118A | 3/1984 | United Kingdom . |
| 0285251 | 2/1988 | United Kingdom . |
| 0304232 | 8/1988 | United Kingdom . |

OTHER PUBLICATIONS

"The Flexible Engine" by Douaud Oil and Enterprise, English and French Version.
Dexter Research Center Technical Description-Model 2M Thermopile Detector.
Dexter Research Center Technical Description-Model DR46 Dual Element Thermopile Detector.
"A Retrofittable Alcohol/Petrol Carburation System", Fourth International Symposium on Alcohol Fuels Technology, Sao Paulo (1980) by Weide et al.
"Vehicle Operation with Variable Methanol/Gasoline Mixtures", VI International Symposium on Alcohol Fuels Technology, Ottawa (1984).
English translation of Netherland Patent No. 8004071, dated Jul. 1981.

Primary Examiner—Carolyn E. Fields
Attorney, Agent, or Firm—Larry W. Evans; David J. Untener; Scott A. McCollister

[57] ABSTRACT

A process for spectroscopically measuring the content of a component in a liquid mixture involves passing a single optical beam through the mixture without the use of a reference beam and measuring the intensities of transmitted light in two different wavelength bands by means of two adjacent detectors responsive to light in the two wavelength bands respectively. The component being measured absorbs light within one of the wavelength bands. The ratio of the detector outputs can then be related to the component concentration. The principal use of the invention is for in-situ measurement of methanol in gasoline for motor vehicles.

14 Claims, 4 Drawing Sheets

OPTICAL MEASUREMENT METHOD USING STACKED GERMANIUM AND SILICONE DETECTORS

This is a continuation of copending application Ser. No. 07/233,630 filed on Aug. 18, 1988, abandoned.

The present invention relates to the measurement of the relative proportions of two liquids where one of the liquids has a significant absorbtion of light in the infra-red.

Examples of mixtures where is is particularly desirable to measure the content of one liquid in another are mixtures of alcohols and liquid hydrocarbons.

Alcohols, e.g. methanol, are desirable clean burning fuels for internal combustion engines. Methanol's clean-burning properties make it desirable for use in those parts of the world where there is a problem with air pollution from the emissions of vehicles powered by internal combustion engines. Methanol can be made from methane which may be available in countries where crude oil derived transportation fuels cannot be produced from internal resources. However, the combustion characteristics of alcohol fuels are different from those of the conventional liquid hydrocarbon fuels (gasoline, diesel fuel) and therefore requires different spark timings and mixture strengths for optimum performance. An engine adjusted to run on pure methanol will not run satisfactorily on liquid hydrocarbon fuels and vice-versa. Vehicles which can only use say pure methanol will not be sold on a large scale unless there is a comprehensive methanol distribution system. A comprehensive methanol distribution network will not be set up until there is a large number of vehicles which are capable of using methanol. There is therefore a need to provide transport vehicles with a system that enables them to use fuels containing varying amounts of alcohol and liquid hydrocarbons and which can adjust the engine settings e.g. the rate at which fuel is fed, in accordance with the composition of the mixture fed to the engine at any given time.

According to the present invention a process for measuring the content of a first component which absorbs light in the infra-red within a first wavelength band in a liquid mixture which also contains a second component which does not significantly absorb light within the first wavelength band, which comprises passing light comprising light within said first wavelength band through the liquid mixture in a cell, generating in a first detector which is responsive to light within said first wavelength band a signal which is related to the intensity of light within first wavelength band transmitted through the liquid mixture is characterised in that:

(1) the light passed through the liquid mixture also comprises light in the infra-red within a second wavelength band which is not significantly absorbed by the first component, and a signal related to the intensity of light in the second wavelength band transmitted through the liquid mixture is generated by a second detector responsive to the light within the second wavelength band and which is stacked with the first detector.

The process of the present invention is particularly useful for measuring the alcohol content in a motor fuel (gasoline); more particularly it is useful for measuring the methanol content in motor fuel.

The detection system may be, for example a Si/Ge detector. Such stacked detectors are commercially available from Judson Infrared Inc.

Fuel cells based upon the present invention are usually located at some point along a fuel line. The cell is preferably an integral part of the fuel line and has corresponding internal and external diameters. The internal diameter of the cell is preferably in the range from 1-10 mm, more preferably in the range 3 to 7 mm. The fuel cells are particularly suited for use in motor vehicles.

The light source is one having a wide emission spectrum covering both wavelength bands absorbed by the two detectors. Both wavelength bands will be in the infra-red preferably in the near infra-red. For the purposes of the present invention, infra-red is understood to mean that portion of the electromagnetic spectrum which corresponds to radiation having a wavelength between 700 and 25,000 nm. and near infra-red is understood to mean that portion of the electromagnetic spectrum which corresponds to radiation having a wavelenght between 700 and 1,700 nm. The light source is preferably an incandescent light source e.g. a filament bulb emitting "white" light, i.e. light covering a continuous spectrum of wavelengths. The "white" incandescent light source maybe under-run (i.e. using a lower than design voltage to maximise life).

Since the first harmonic of an infra-red vibration has a stronger absorption than the second harmonic, the present invention is preferably operated with a light source and detector system adapted for use with light of a wavelength corresponding to the first harmonic of the O-H stretching frequency of the sample alcohol (1,400-1,600 nm). This will necessarily facilitate use of a shorter cell path lenght. Using systems adapted for use with light of a wavelength corresponding to the second harmonic (900-1000 nm) will therefore necessitate longer cell path lengths (>5cm) because of the weaker absorption of the radiation. Longer cell path lengths not only increase noise to signal ratios but also result in less compact cells.

It is particularly preferred to use a light source with a lens to give a concentrated beam of light so as to reduce optical losses and improve signal to noise ratio. Incandescent bulbs with built-in lenses are readily available and the possibility of using such cheap readily available light sources is an important advantage of the invention.

The use of a stacked detection system comprising two detectors adjacent to each other and responsive to two different wavelength bands provides good compensation for any changes in the transmission of light through the liquid which are not due to changes in the amount of the component which absorbs infra-red light for example dirt on windows. Such changes will affect both wavelength bands equally so that the ratio of the two outputs from the two detectors will be independent of such changes. Some compensation will be provided in this way for changes in light intensity of the incandescent bulb caused for example by lamp ageing.

The performance of the device can be improved by placing an interference filter in the light path between the light source and the detectors. The interference filter is selected so as to pass light only at certain multiples of a given wavelength corresponding to the required measurement and reference wavelengths. The effect of this is to increase the measurement sensitivity and reduce the sensitivity to other interfering effects such as shift in detector band gap edge with temperature.

The accuracy of the device may be further improved by modulating the light source so that its intensity varies at regular intervals. This may be done by using a sinusoidally modulated power source or by using a mechanical chopper to interrupt the light beam. Sinusoidally modulating the light source is to be preferred since it results in increased lamp lifetime.

The spectral output of the ight source may change slightly as the lamp ages. An additional detector or second detection system (e.g. stacked detector) may be placed adjacent to the lamp in order that the output may be used to modify either the power supply to the lamp or the sensor output to correct for any such spectral changes.

The invention may be applied to the control of an internal combustion engine using a mixture of alcohol and hydrocarbon as fuel. Suitable circuitry for adjusting the settings of fuel metering systems, such as carburettors and fuel injection equipment, ignition systems and pressure charging devices in accordance with measurements of the amount of alcohol in the fuel are well known to those skilled in the art.

In addition, the engine management systems as described above may be used if necessary to compensate for variations in absorbance measurement with temperature. However, such variations will not be significant in the cooler under-the-bonnet regions e.g. near the dashboard.

The invention is illustrated by the accompanying drawings.

Figure 1:
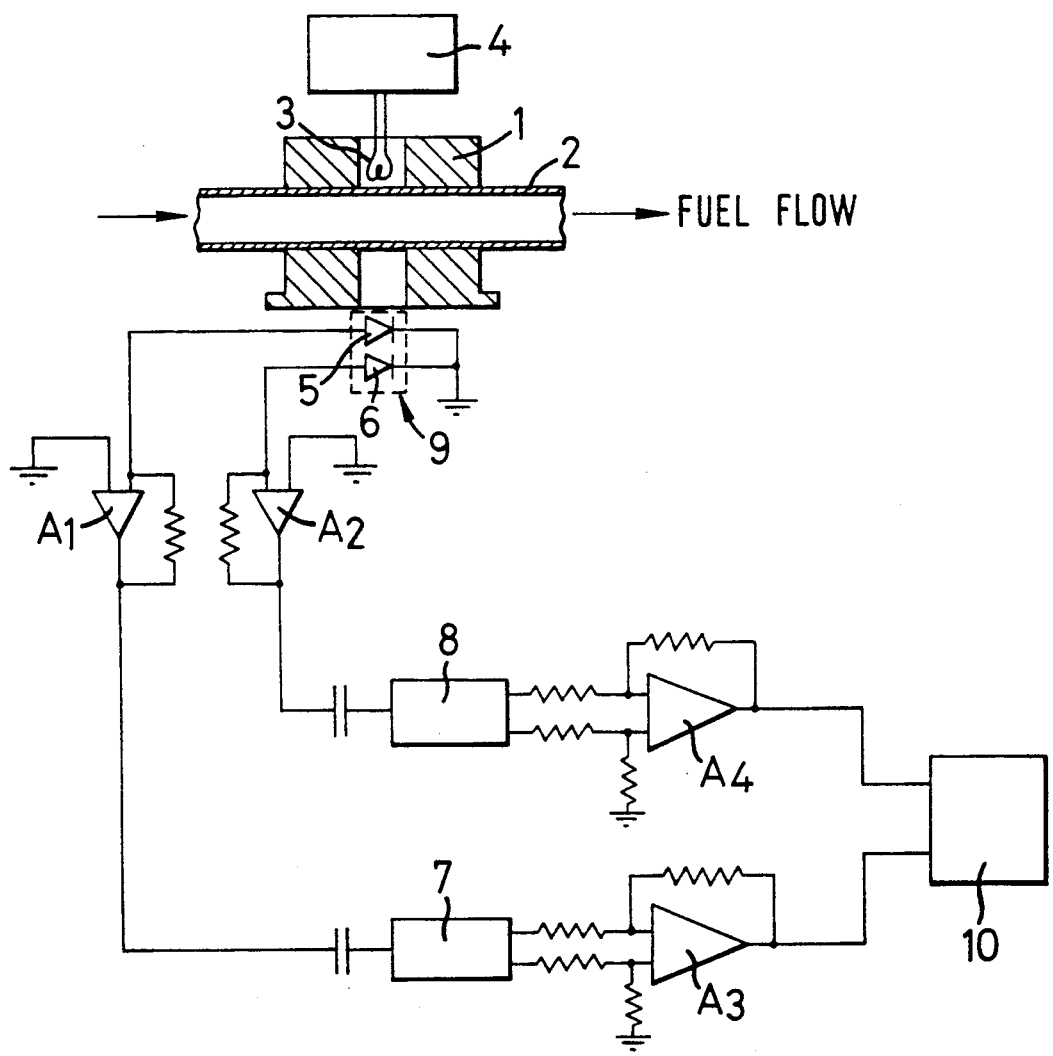
FIG. 1 is a simplified cross-sectional view of the methanol sensor together with a diagrammatic representation of some of the associated electronic circuitry.

In FIG. 1, the sensor body 1 houses the fuel flow cell 2, the light source 3, photodetectors 5 and 6, and the detector pre-amplifiers $A_1$, $A_2$. The sensor body is typically made from a material suitable for harsh environments e.g. nylon. The fuel flow cell 2 is equipped with suitable couplings (not shown) so as to facilitate attachment to fuel lines. The cell is constructed out of a fuel resistant material preferably transparent to near infrared radiation so as to eliminate the necessity for windows. Such a material might be polyethersulphone.

The light source consists of a tungsten filament lamp 3 with a lifetime in excess of 5000 hours. The lamp is driven at very low frequency e.g. 5 Hz by for example a Wien bridge sine-wave oscillator 4.

The detector unit, which is located directly opposite the light source 3, on the other side of the fuel flow cell 2, comprises two photodetectors 5 and 6. The photodetector nearest the light source 3 is a silicon photodetector 5 and the one furthest away from the light source 3 is a germanium photodetector 6. The two photodetectors 5 and 6 may be incorporated into a single dual wavelength photodetector 9 e.g. Judson J16Si silicon on germanium detector where the two photodetectors are stacked one adjacent to the other.

The signal from photodetectors 5 and 6 is then amplified by means of the preamplifiers $A_1$ and $A_2$. The ac signals from $A_1$ and $A_2$ are then processed by means of peak to peak detectors 7 and 8 and difference amplifiers $A_3$ and $A_4$ to give a dc signal which is fed to an analogue divider 10 before giving a dc output signal. This electronic processing is well known to those skilled in the art.

The final dc output signal is then fed to an electronic management system designed to alter the running conditions of an engine in accordance with the fuel composition. Such electronic management systems are well known to those skilled in the art.

Figure 2:
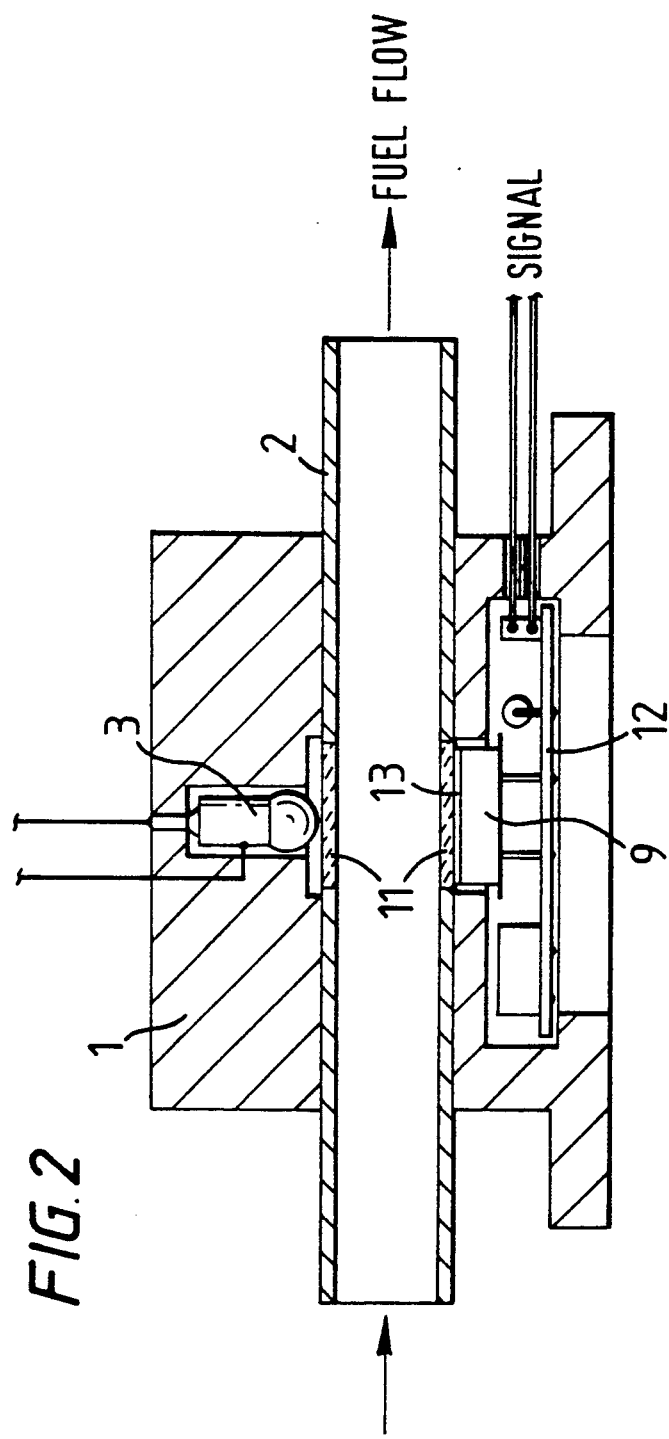
FIG. 2 is a more detailed cross-sectional view of one possible embodiment of the sensor.

Referring now to FIG. 2 the sensor housing 1 contains the fuel flow cell 2 which has a 5 mm internal diameter, a light source 3 as described in FIG. 1, a dual wavelength photodetector system 9 and the associated electronic circuitry 12. Incorporated into either side of the fuel flow cell 2 and in between the light source 3 and photodetector 9 are two optical windows 11 giving high transmission in the region 800 to 1700 nm. (Alternatively the cell itself may be constructed from material with high transmission in this region.) An optical filter 13 is located in between either the photodetector system 9 and fuel flow cell 2 or the light source 3 and fuel flow cell 2, in order to enhance the sensitivity of the measurement by transmitting light only at pass bands centred on 1550 nm and 775 nm.

The detector preamplifiers $A_1$ and $A_2$ as described in FIG. 1 are built into a circuit board 12, the output being taken to another circuit board housed in another box (not shown) which contains the remaining signal processing circuitry as described (in simplified form) in FIG. 1.

In addition another embodiment of the sensor giving greater precision may incorporate a second detector or detection system (not shown) positioned adjacent to the light source such that it acts as a monitor of light source output, compensating for spectral shifts.

Figure 3:
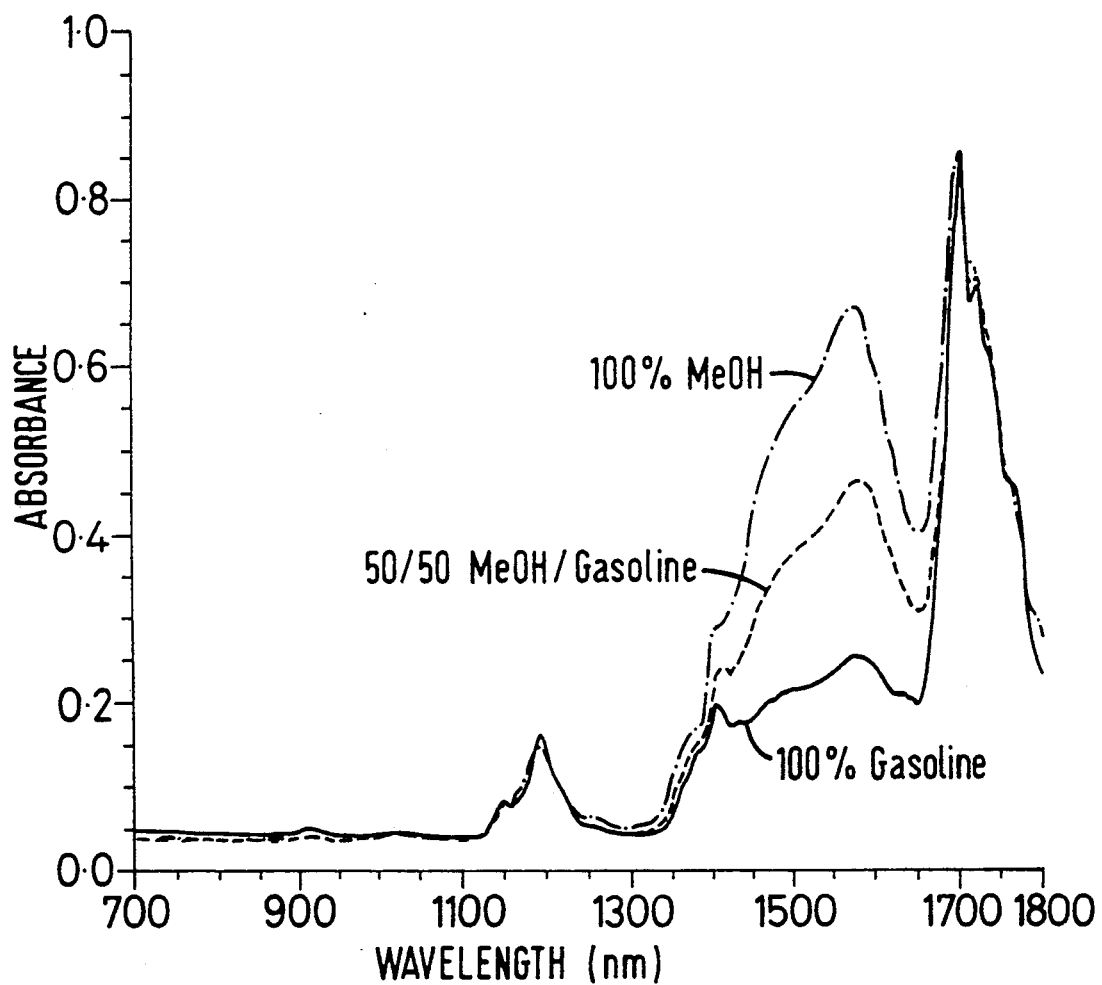
FIG. 3 illustrates the absorbance characteristics of methanol, gasoline and 50/50 methanol/gasoline as a function of a wavelenght.

FIG. 3 shows that there is a wavelength at around 1500nm where the absorbance is very strongly dependent on the relative amounts of methanol and gasoline, while there are other wavelengths, e.g., below 1100nm, where the relative amounts of methanol and gasoline has very little effect on the absorbance.

Figure 4:
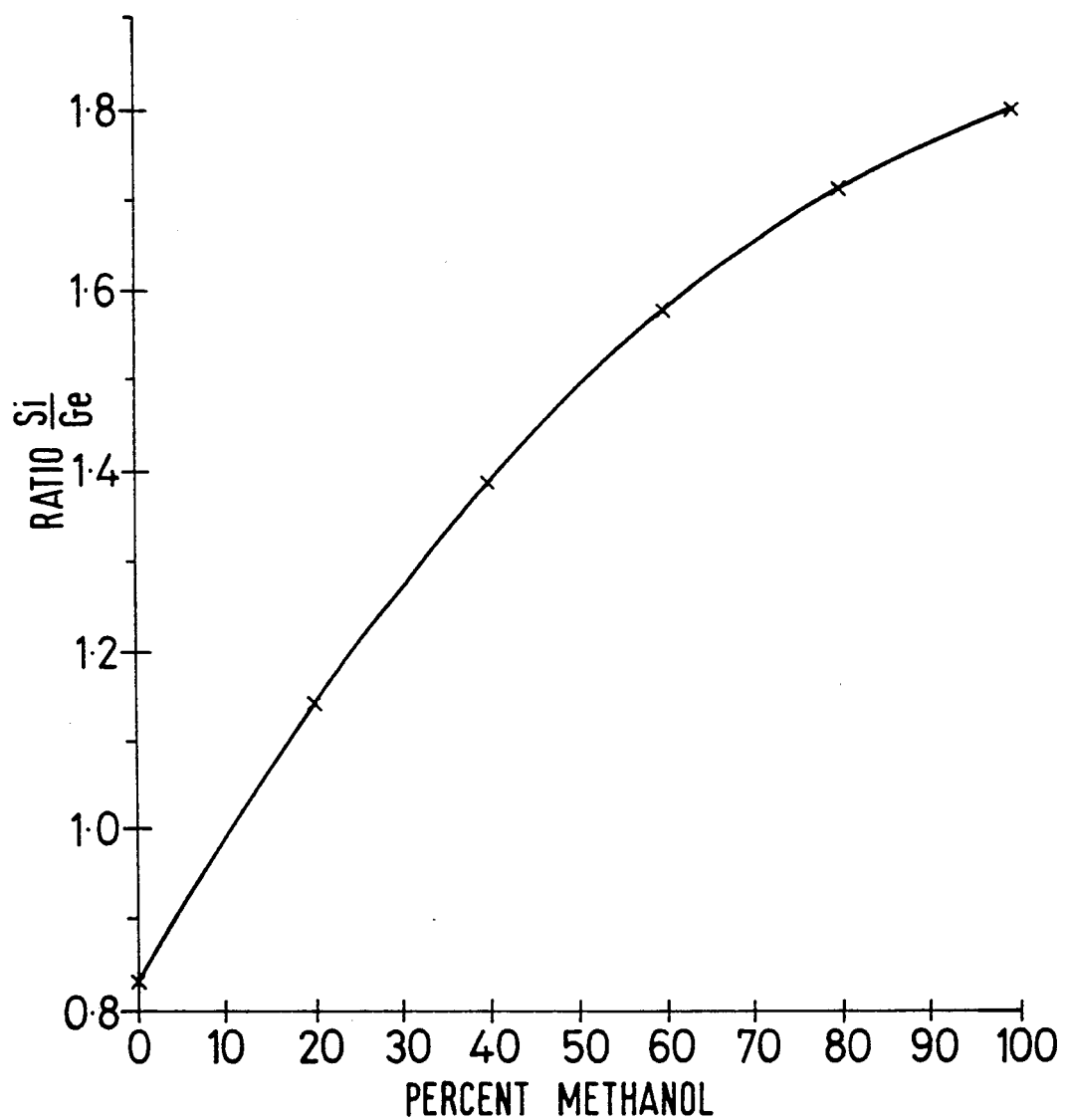
FIg. 4 is a plot of change in the ratio of the detector outputs (Si/Ge) with change in methanol/gasoline ratio. The full range of methanol concentration has been covered.

FIG. 4 shows that there is a smooth change in the ratio of the signals from the silicon and germanium detectors with changes in the proportion of methanol in a methanol/gasoline mixture, showing that the ratio of two detectors gives a good measurement of the methanol content.

We claim:
1. A process for measuring the content of a first component in a liquid mixture;
   said first component absorbing light in the infra-red within a first wavelength band,
   said liquid mixture comprising a second component, said second component not significantly absorbing light within said first wavelength band,
   which process comprises:
   (a) passing light through said liquid mixture in a cell, said light comprising light within said first wavelength band and light within a second wavelength band, light from said second wavelength band not being significantly absorbed by said first component, and
   (b) generating signals related to the intensities of the light transmitted through the liquid in the first and second wavelength bands by means of first and second detectors, each individually responsive to light within the first and second wavelength bands respectively, said first detector being a germanium photodetector and said second detector being a silicon photodetector, and the second detector being stacked above said first detector.

2. A process as defined in claim 1 wherein the first component is an alcohol and the second component is a liquid hydrocarbon.

3. A process as defined in claim 2 wherein the alcohol is methanol.

4. A process as claimed in claim 1 wherein the wavelength bands fall within the region 700 to 1,700 nm.

5. A process as claimed in claim 1 wherein the light source covers both first and second of wavelength bands.

6. A process as claimed in claim 5 such that a lens is interposed between the light source and the detectors so as to concentrate the beam of light.

7. A process as claimed in claim 5 wherein an interference filter is interposed between the light source and the detectors so as to pass light at certain multiples of a specified wavelength.

8. A process as claimed in claim 2 wherein at least one wavelength band corresponds to the first harmonic of the O—H stretching frequency of said alcohol.

9. A process as claimed in claim 2 including processing said signals to measure the content of said alcohol in said liquid mixture.

10. A process as claimed in claim 9 including compensating for variations in said signals with temperature.

11. A process as claimed in claim 2 including adjusting at least one control of an internal combustion engine in accordance with the content of said first component in said liquid mixture.

12. A process as claimed in claim 1 including compensating for spectral changes in the source of said light.

13. A process as claimed in claim 1 including varying light intensity at regular intervals.

14. A process as claimed in claim 2 for determining the methanol content of hydrocarbon/methanol liquid fuel fed to an automobile engine wherein said light is passed through a fuel line leading to the automobile engine from a source on one side of the fuel line to the first and second detectors on the other side of the fuel line.

* * * * *